United States Patent
Brokish

(10) Patent No.: US 6,642,441 B2
(45) Date of Patent: Nov. 4, 2003

(54) INBRED CORN LINE KW4773

(75) Inventor: Harold A. Brokish, Champaign, IL (US)

(73) Assignee: KWS Kleinwanzlebener Saatzucgt AG (DE)

( * ) Notice: Subject to any disclaimer, the term of this patent is extended or adjusted under 35 U.S.C. 154(b) by 0 days.

(21) Appl. No.: 10/052,254

(22) Filed: Jan. 23, 2002

(65) Prior Publication Data

US 2003/0154522 A1 Aug. 14, 2003

(51) Int. Cl.$^7$ ............ A01H 5/00; A01H 4/00; A01H 1/00; A01H 1/02; C12N 15/82
(52) U.S. Cl. ............ 800/320.1; 800/260; 800/265; 800/266; 800/267; 800/268; 800/269; 800/278; 800/279; 800/281; 800/284; 800/302; 800/303; 800/275; 800/300.1; 435/69.1; 435/412; 435/424; 435/430; 435/430.1; 435/419; 435/468; 435/421
(58) Field of Search .............. 800/265, 266, 800/260, 267, 268, 278, 320.1, 269, 275, 279, 281, 284, 302, 303, 300.1; 435/412, 419, 421, 424, 430, 430.1, 468, 69.1

(56) References Cited

U.S. PATENT DOCUMENTS 5,523,520 A * 6/1996 Hunsperger et al. ........ 800/200
5,773,683 A * 6/1998 Foley ......................... 800/200

OTHER PUBLICATIONS

Kraft et al. Theor. Appl. Genet. 2000, vol. 101, pp. 323–326.*

Eshed et al. Genetics. 1996, vol. 143, pp. 1807–1817.*

* cited by examiner

Primary Examiner—David T. Fox
Assistant Examiner—Medina A. Ibrahim
(74) Attorney, Agent, or Firm—Jondle & Associates PC

(57) ABSTRACT

This invention is in the field of corn breeding, specifically relating to a dent corn inbred designated as KW4773. Inbred KW4773 is a stiff stalk family based inbred that is specifically bred by a pedigree selection method for the north central United States. Inbred KW4773 contributes superior grey leaf blight resistance to the F1 hybrid.

21 Claims, No Drawings

INBRED CORN LINE KW4773

FIELD OF THE INVENTION

This invention is in the field of corn breeding, specifically relating to a dent corn inbred designated as KW4773. Inbred KW4773 is a stiff stalk family based inbred that is specifically bred by means of a pedigree selection method for the north central United States. As one of the parents, Inbred KW4773 contributes superior grey leaf blight resistance to the F1 hybrid. When appropriate industry standards that use a stiff stalk family based inbred as one of the parents are compared to an F1 with KW4773 as one of the parent lines, the grey leaf blight resistance resulting from the genetics of KW4773 is readily apparent.

BACKGROUND OF THE INVENTION

The present invention relates to a new and distinctive corn inbred line, designated KW4773. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals.

The goal of plant breeding in corn is to develop inbred parent lines that contribute various desirable traits to the hybrids in which they are used. These traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, stalk strength, root strength, ear retention, maturity and plant and ear height, are important.

Choice of breeding or selection methods depends on the mode of plant reproduction, the heritability of the trait(s) being improved, and the type of cultivar used commercially (e.g., F.sub 1 hybrid cultivar, pureline cultivar, etc.) For highly heritable traits, a choice of superior individual plants evaluated at a single location will be effective, whereas for traits with low heritability, selection should be based on mean values obtained from replicated evaluations. Popular selection methods commonly include pedigree selection, modified pedigree selection, mass selection, and recurrent selection.

Field crops can be bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produces a uniform population of hybrid plants that may be heterozygous for many gene loci. A cross of two plants each heterozygous at a number of loci will produce a population of hybrid plants that differ genetically and will not be uniform.

Corn plants (Zea mays L.) can be bred by both self-pollination and cross-pollination techniques. Corn has separate male and female flowers on the same plant, located on the tassel and the ear respectively. Natural pollination occurs in corn when the wind blows pollen from the tassels to the silks that protrude from the tops of the incipient ears.

The development of corn hybrids requires the development of homozygous inbred lines, the crossing of these lines, and the evaluation of the crosses. The goal of plant breeding is to develop new, unique and superior corn inbred lines and hybrids. In pedigree selection breeding, the breeder combines the genetic backgrounds of two or more inbred lines or various broad-based sources into breeding pools from which the new inbred lines are developed by selfing and selection of the desired phenotypes. The new inbreds are crossed with other inbred lines and the hybrids from these crosses are thoroughly tested and compared to appropriate standards in environments representative of the commercial target area(s).

Pedigree selection breeding starts with the crossing of two genotypes, each of which may have one or more desirable traits or more desirable characteristics that are lacking in the other or which complement the other. If the two original parents do not provide all of the desired characteristics, other sources can be included in the breeding population. In the pedigree selection method, superior plants are selfed and selected in successive generations. In the succeeding generations, the heterozygous condition gives way to the homozygous lines as a result of self-pollination and selection. Typically in the pedigree method of breeding, five or more generations of selfing and selection are practiced: F1; F2; F3; F4; F5, etc. These selfing generations are sometimes designated as S0, S1, S2, etc with S0 being an equivalent to F1 while S2 is an equivalent to F3, etc.

Descriptions of breeding methods that are commonly used for different traits and crops can be found in one of several reference books (e.g., Allard, R. W. "Principles of Plant Breeding" John Wiley and Son, pp. 115–161, 1960; Simmonds, 1979; Sneep et al., 1979; Fehr, 1987).

A single cross corn hybrid is the cross of two inbred parent lines, each of which has a genotype which compliments the genotype of the other. The hybrid progeny of the first generation is designated F1. In the development of hybrids, only the F1 hybrid plants are sought. Preferred F1 hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, breed true and are highly uniform; and (3) crossing the selected inbred lines with unrelated inbred lines to produce the hybrid progeny (F1). During the inbreeding process in corn, the vigor of the lines decreases. Vigor is restored when two unrelated inbred lines are crossed to produce the hybrid progeny (F1). An important consequence of the homozygosity and homogeneity of the inbred lines is that the hybrid between any two inbreds will always be the same. Once the inbreds that give a superior hybrid have been identified, the hybrid seed can be produced indefinitely as long as the homogeniety of the inbred parents is maintained.

A single cross hybrid is produced when two inbred lines are crossed to produce the F1 progeny. Much of the hybrid vigor exhibited by F1 hybrids is lost in the next generation (F2). Consequently, seed from hybrid varieties is not used for planting stock.

Corn is an important and valuable field crop. Thus, a continuing goal of plant breeders is to develop consistent performing, high-yielding corn hybrids that are agronomically sound based on stable inbred lines. The reasons for this goal are obvious: to maximize the amount of grain produced with the inputs used and to minimize susceptibility of the crop to environmental stresses. To accomplish this goal, the corn breeder must select and develop superior inbred parental lines for producing hybrids. This requires identification and selection of genetically unique individuals which in a segregating population occur as a result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if an entire genotype of the parents has been characterized and the desired genotype is know, only a few, if any, individuals having the desired genotype may be found in a large F2 or S1 population. Typically, however, the genotype of neither the parents nor the desired genotype is known in any detail. An agronomically acceptable F1 hybrid will come from a cross between two superior inbred parental lines. There is no assurance that either of these parental lines will produce a superior hybrid when crossed with a different inbred parent line. Thus, the selection or combination of the two parental inbreds provides a unique hybrid that demonstrates characteristics and performance levels that differ from that obtained when either of the parents is crossed with a different inbred parent line.

Once the superior combination of two parental lines is determined by the testing and selection of the F1 hybrid, that F1 hybrid and the performance traits and characteristics of the hybrid can be indefinitely reproduced so long as the parental inbreds are maintained in their homozygosity and the quality and production procedures are accomplished to the purity standards determined by the seed industry regulations.

SUMMARY OF THE INVENTION

This invention provides for a novel inbred corn line designated as KW4773. This invention thus relates to the seeds of inbred corn line KW4773. The invention also includes the corn plants produced by the seed of KW4773 and other plants resulting from all or part of the genetics of KW4773 and other resulting hybrids in which KW4773 is one of the parents. In addition, this invention provides for a corn plant having the physiological and morphological characteristics of inbred KW4773.

This invention also provides for the tissue cultures of regenerable cells of a plant derived directly from inbred KW4773 especially where the tissue regenerates into plants having all or essentially all of the important morphological and physiological characteristics of inbred KW4773. The plants regenerated from the tissue culture cells derived from inbred KW4773 are also a part of this invention.

Inbred seed or hybrid seed produced utilizing the genetic contributions of a plant or plants derived from inbred KW4773 are expressly included in this invention.

The inbred corn plant of the invention may further comprise, or have, a cytoplasmic factor, or other factor, that is capable of conferring male sterility. So, the invention further comprises a male sterile form of the inbred. Parts of the corn plant of the present invention are also provided, such as e.g., pollen obtained from an inbred plant and an ovule of the inbred plant.

Another objective of the invention is to provide methods for producing other inbred corn plants derived from inbred KW4773. Inbred corn lines derived by the use of those methods are also part of the invention.

The invention also relates to methods for producing a corn plant containing in its genetic material one or more transgenes and to the transgenic corn plant produced by that method.

In another aspect, the present invention provides for single gene converted plants of KW4773. The single transferred gene may preferably be a dominant or a recessive allele. Preferably, the single transferred gene will confer such trait as male sterility, herbicide resistance, insect resistance, resistance for bacterial, fungal, or viral disease, male fertility, enhanced nutritional quality and industrial usage. The single gene may be a naturally occurring maize gene or a transgene introduced through genetic engineering techniques.

The invention further provides for developing a corn plant in a corn plant breeding program using plant breeding techniques including recurrent selection, backcrossing, pedigree breeding, restriction fragment length polymorphism enhanced selection, genetic marker enhanced selection and transformation, and haploid induction and dihaploid formation. Seed, corn plant, and parties thereof produced by such breeding methods are also part of the invention.

DEFINITIONS

In the description and tables that follow, a number of terms are used. In order to provide a clear and consistent understanding of the specification and claims, including the scope to be given such terms, the following definitions are provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Essentially all the physiological and morphological characteristics. A plant having essentially all the physiological and morphological characteristics means a plant having the physiological and morphological characteristics, except for the characteristics derived from the converted gene.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Predicted RM. This trait for a hybrid, predicted relative maturity (RM), is based on the harvest moisture of the grain. The relative maturity rating is based on a known set of checks and utilizes conventional maturity such as the Comparative Relative Maturity Rating. System or its similar, the Minnesota Relative Maturity Rating System.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Yield (Bushels/Acre). The yield is recorded in bushels per acre of the harvested grain after adjusting to a 15% moisture basis.

Moisture. The moisture is the percent grain moisture recorded at the time of harvest. All hybrids in a test are harvested and moistures are recorded in succession to insure that there is no appreciable change in conditions from the recording of the first hybrid in the test to the recording of the last hybrid in the test.

Growing Degree Units—GDU. Growing degree units (GDU) are heat units as calculated by the Barger Method. The temperature maximum and minimums are based on a 24-hour period. Calculations are from planting. GDU is equal to the maximum temperature plus the minimum temperature divided by two and subtract 50. If the maximum temperature is more than 86 degrees then the maximum temperature is 86. If the minimum temperature is less than 50 degrees then the minimum temperature will be 50. GDU's are a way of measuring plant maturity.

Stalk Lodging. Stalk lodging is a percentage of stalk lodged plants compared to the total number of plants in a plot. A stalk lodged plant is defined as a plant that is breaking over at a point below the upper ear node of attachment.

Root Lodging. Root lodging is a percentage of root lodged plants compared to the total number of plants in a plot. A root lodged plant is defined as a plant that has the main stalk deviate from vertical at an approximate angle of 30 degrees or more.

Plant Height. This is a measure of the height of the hybrid from the ground to the tip of the tassel, and is measured in centimeters.

Ear Height. The ear height is a measure from the ground to the ear node attachment, and is measured in centimeters.

Population. The population is a physical count of the number of plants in a plot and is expressed as the population equivalent per acre or number of plants per acre.

Test Weight. The test weight is recorded in pounds per bushel. It is a measure of the specific density of the harvested grain.

Relative Maturity. Relative maturity is based on the Minnesota Relative Maturity Rating (MN RM) standard for computing relative maturity.

DETAILED DESCRIPTION OF THE INVENTION

According to the invention, there is provided a novel dent corn parent inbred, designated KW4773. Inbred KW4773 is a stiff stalk family based inbred that has been specifically bred for the north central United States. In addition to matching or exceeding the phenotypes of the other segregates with regard to yield, vigor and the various commercially important agronomic traits, inbred KW4773 also has superior resistance to grey leaf blight when compared in an F1 hybrid to appropriate industry standards that use a stiff stalk family based inbred as one of the parents. This unexpected highly favorable level of grey leaf blight resistance discovered in KW4773 directly relates to significantly improved grey leaf blight resistance in the F1 hybrids resulting in improved yield and plant health in the presence of grey leaf blight.

Grey leaf blight has become an increasing concern in the north central United States because of the increased practice of minimal tilling. The practice of minimal tilling has become increasingly common in order to minimize soil loss due to erosion and to reduce fuel consumption required in more extensive tilling. However this practice tends to increase last years leaf debris on the surface of the soil. This debris serves as a source of carryover inoculum for grey leaf blight. In the past, conventional tilling practices would have buried last years plants and the current year's corn exposure to any inoculum would be minimized.

This inbred, KW4773, is a homozygous inbred developed by pedigree selection. The inbred, KW4773, has shown uniformity and stability for the traits, as described in the following inbred description information. It has been self-pollinated a sufficient number of generations with careful attention to uniformity of the plant type. The inbred has been increased with continued observations for uniformity. No variant traits have been observed or are expected in KW4773. Inbred corn line, KW4773 has the following morphological characteristics and is compared to the morphological characteristics of a commonly known stiff stalk family inbred, B73.

INBRED DESCRIPTION INFORMATION

All colors follow the Munsell Color Code. Angles are recorded in degrees. Linear measurements and weights are recorded in the appropriate metric units.

TABLE 1

| TRAIT | KW4773 |
|---|---|
| Type | Dent |
| Region Where Developed | North Central USA |
| GDU 50% Pollen | 1511 |
| GDU 50% Silk | 1540 |

Growing Degree Units=GDU=Heat Units as calculated by the Barger Method. The temperature maximum and minimums are based on a 24-hour period. Calculations are from Planting.

$$GDU = ((\text{Max Temp} + \text{Min Temp})/2) - 50$$

If Max Temp is >86 degrees, then Max Temp=86
If Min Temp is <50 degrees, then Min Temp=50

| PLANT | |
|---|---|
| Plant Height, Soil to Tassel Tip | 203.2 cm |
| Ear Height, Upper Ear Attachment | 83.8 cm |
| Length of Top Ear Internode | 14.1 cm |
| Number of Tillers | 0 |
| Anthocyanin of Brace Roots | Moderate |
| LEAF | |
| Width of Ear Node Leaf | 9.3 cm |
| Length of Ear Node Leaf | 75 cm |
| No. of Leaves Above Top Ear | 5 |
| Leaf Angle from the Stalk, $2^{nd}$ Leaf Above Ear | 20 Degrees |
| Leaf Color | 5-4/4 |
| Leaf Sheath Pubescense (1 = None, 9 = Like Peach Fuzz): | 4 |
| Marginal Waves on Leaf (1 = None, 9 = Many): | 4 |
| Longitudinal Leaf Creases (1 = None, 9 = Many): | 2 |

-continued

TASSEL

| | |
|---|---|
| Number of Lateral Branches | 4 |
| Branch Angle from Central Spike | 20 Degrees |
| Tassel Length (Top Leaf Collar to Tassel Tip): | 41 cm |
| Pollen Shed | 7 |
| (0 = Male Sterile, 9 = Heavy Shed): | |
| Anther Color | 10Y9/8 |
| Glume Color | 5GY5/6 |

EAR: (UNHUSKED)

| | |
|---|---|
| Silk Color 3 Days after Emergence: | 10Y9/6 |
| Fresh Husk Color, 25 Days after 50% Silking: | 5GY5/8 |
| Dry Husk Color, 65 Days after 50% Silking: | 5Y8.5/6 |
| Position of Ear | Upright |
| Husk Tightness | 2 |
| (1 = Very Loose, 9 = Very Tight): | |
| Husk Extension at Harvest | Medium |

EAR: (HUSKED)

| | |
|---|---|
| Ear Length | 16.2 cm |
| Ear Diameter at Mid-Point | 43 mm |
| Ear Weight | 96 grams |
| Number of Kernel Rows, Mid-Ear | 18 |
| Kernel Rows Alignment | Straight |
| Shank Length | 10.3 cm |
| Ear Taper | Conical |

KERNEL: (DRIED)

| | |
|---|---|
| Kernel Length | 11 mm |
| Kernel Width | 7.5 mm |
| Kernel Thickness | 4.7 mm |
| Round Kernels, (Shape Grade) | 22% |
| Aleurone Color Pattern | Homozygous |
| Hard Endosperm Color | 10YR7/12 |
| Weight per 100 Kernels | 30 gm |

COB

| | |
|---|---|
| Cob Diameter at Mid-Point | 25.5 mm |
| Cob Color | Red |

DISEASE EVALUATION RATINGS

Disease evaluation ratings were conducted by Professional Seed Research, Inc., 7 South 437 Dugan Road, Sugar Grove, Ill. 60554. The evaluations are listed in Table 2. These evaluations indicate the grey leaf blight ratings for KW4773 and other stiff stalk family inbreds crossed a standard inbred line to form F1 hybrids.

One parent, LH185, is in common in all F1 hybrid combinations. This would indicate that the differences observed in the to resistance to grey leaf blight is attributed to the inbreds that are not in common in all the F1 hybrids. The F1 hybrid with KW4773 as one of the parent lines was appreciably higher in resistance to grey leaf blight than any of the other F1 hybrids. This leads to the conclusion that the invention KW4773 is superior in resistance to grey leaf blight and that as one of the parents in an F1 hybrid, KW4773 contributes this resistance to the F1 hybrid.

Ratings are taking from replicated plots. The ratings are recorded on two separate observation dates.

DEFINITIONS FOR TABLE 2

Grey Leaf Blight=Grey Leaf Spot, *Cercospora zeae-maydis*
RATING SCALE:
1=Highly resistant, resulting in no lesions when inoculated.
2=Resistant reaction, limiting the pathogen to only a few limited sized lesions.
3=Intermediate, will look bad visually, but no significant performance damage.
4=Susceptible reaction, performance damage will result at this level.
5=Extremely susceptible, significant yield loss and stalk damage are expected.

TABLE 2

GREY LEAF BLIGHT RATING DATA

| HYBRID | RATING 1 | RATING 2 | AVERAGE |
|---|---|---|---|
| FR1064 × LH185 | 4 | 3 | 3.5 |
| KW4621 × LH185 | 4 | 4 | 4.0 |
| KW4634 × LH185 | 4 | 4 | 4.0 |
| KW4612 × LH185 | 4 | 3 | 3.5 |
| KW4773 × LH185 | 2 | 2 | 2.0 |

Based on the above study, KW4773 contributes significantly higher levels of resistance to grey leaf blight in the F1 hybrid. Plant health as it relates to disease resistance can have effects on the yield performance of the F1 hybrid.

Table 3, Table 4 and Table 5 list the results from the replicated performance trials. In Table 3 and 4, data is recorded to compare an F1 hybrid using KW4773 as one of the parents with some of the commercially know hybrids. In Table 5, the results also make some direct comparisons in which one parent line, LH185, is in common in all of the hybrids. The observed differences in the performance of the respective F1 hybrids can be attributed to the opposite parent.

Listed below are the column headings for Tables 3–5 and their definitions.

1. LOCATION is defined as a testing environment.
2. YIELD is recorded in bushels per acre of the harvested grain after adjusting to a 15% moisture basis.
3. MOIS is the percent grain moisture recorded at the time of harvest. All hybrids in a test are harvested and moistures are recorded in succession to insure that there is no appreciable change in conditions from the recording of the first hybrid in the test to the recording of the last hybrid in the test.
4. % RL is based on the actual count of root lodged plants relative to the total number of plants in a plot. A root lodged plant is defined as a plant that has the main stalk deviate from vertical at an approximate angle of 30 degree or more.
5. % SL is based on the actual count of stalk lodged plants relative to the total number of plants in a plot. A stalk lodged plant is defined as a plant that is breaking over at a point below the upper ear node of attachment.
6. POP'N is a physical count of the number of plants in a plot and is expressed as the population equivalent per acre or number of plants per acre.
7. TW is Test Weight. This is recorded in pounds per bushel. It is actually a measure of the specific density of the harvested grain.

TABLE 3

Hybrid Comparisons from Replicated Data
2001
170 Replications   25 Locations
4 Row Plots   Center 2 Harvested for Data

| HYBRID | YIELD | MOIS | % RL | % SL | POP'N | TW |
|---|---|---|---|---|---|---|
| KW4773 × LH185 | 182.6 | 18.5 | 7.1 | 7.3 | 27,975 | 53.2 |
| HC33 × LH287 | 181.8 | 18.1 | 6.0 | 10.6 | 28,091 | 55.1 |

TABLE 3-continued

Hybrid Comparisons from Replicated Data
2001
170 Replications  25 Locations
4 Row Plots  Center 2 Harvested for Data

| HYBRID | YIELD | MOIS | % RL | % SL | POP'N | TW |
|---|---|---|---|---|---|---|
| P33G26 | 176.0 | 18.5 | 3.7 | 8.8 | 27,978 | 56.9 |
| HC33 × LH283 | 170.9 | 18.4 | 5.5 | 10.5 | 27,852 | 56.4 |

TABLE 4

Hybrid Comparisons from Replicated Data
2000
16 Locations
4 Row Plots  Center 2 Harvested for Data

| HYBRID | YIELD | MOIS | % RL | % SL | POP'N | TW |
|---|---|---|---|---|---|---|
| KW4773 × LH185 | 172.9 | 15.2 | 6.7 | 20.8 | 31,490 | 54.1 |
| P3335 | 171.1 | 15.0 | 1.8 | 20.7 | 32,070 | 56.9 |
| P33G26 | 169.3 | 15.4 | 0.7 | 18.4 | 32,320 | 54.3 |
| HC33 × LH283 | 169.2 | 15.9 | 2.1 | 18.3 | 32,010 | 57.7 |
| LH195 × LH185 | 161.7 | 16.7 | 1.9 | 21.4 | 31,910 | 55.2 |

TABLE 5

Hybrid Comparisons from Replicated Data
2000
21 Locations
4 Row Plots  Center 2 Harvested for Data

| HYBRID | YIELD | MOIS | % RL | % SL | POP'N | TW |
|---|---|---|---|---|---|---|
| KW4773 × LH185 | 176.9 | 14.9 | 2.4 | 17.1 | 32,460 | 53.9 |
| FR1064 × LH185 | 164.6 | 14.7 | 4.2 | 14.2 | 32,310 | 54.8 |
| LH244 × LH185 | 173.5 | 15.1 | 5.0 | 14.5 | 32,210 | 55.3 |
| LH195 × LH185 | 167.5 | 15.3 | 3.8 | 15.8 | 31,790 | 55.1 |

FURTHER EMBODIMENTS OF THE INVENTION

This invention also is directed to methods for producing a corn plant by crossing a first parent corn plant with a second parent corn plant wherein either the first or second parent corn plant is an inbred corn plant of the line KW4773. Further, both first and second parent corn plants can come from the inbred corn line KW4773. Still further, this invention also is directed to methods for producing an inbred corn line KW4773-derived corn plant by crossing inbred corn line KW4773 with a second corn plant and growing the progeny seed, and repeating the crossing and growing steps with the inbred corn line KW4773-derived plant from 0 to 7 times. Thus, any such methods using the inbred corn line KW4773 are part of this invention: selfing, backcrosses, hybrid production, crosses to populations, and the like. All plants produced using inbred corn line KW4773 as a parent are within the scope of this invention, including plants derived from inbred corn line KW4773. Advantageously, the inbred corn line is used in crosses with other, different, corn inbreds to produce first generation ($F_1$) corn hybrid seeds and plants with superior characteristics.

It should be understood that the inbred can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which corn plants can be regenerated, plant calli, plant clumps and plant cells that are intact in plants or parts of plants, such as embryos, pollen, ovules, flowers, kernels, ears, cobs, leaves, husks, stalks, roots, root tips, anthers, silk and the like.

Duncan, et al., *Planta* 165:322–332 (1985) reflects that 97% of the plants cultured that produced callus were capable of plant regeneration. Subsequent experiments with both inbreds and hybrids produced 91% regenerable callus that produced plants. In a further study in 1988, Songstad, et al., *Plant Cell Reports* 7:262–265 (1988), reports several media additions that enhance regenerability of callus of two inbred lines. Other published reports also indicated that "nontraditional" tissues are capable of producing somatic embryogenesis and plant regeneration. K. P. Rao et al., *Maize Genetics Cooperation Newsletter*, 60:64–65 (1986), refers to somatic embryogenesis from glume callus cultures and B. V. Conger, et al., *Plant Cell Reports*, 6:345–347 (1987) indicates somatic embryogenesis from the tissue cultures of corn leaf segments. Thus, it is clear from the literature that the state of the art is such that these methods of obtaining plants are, and were, "conventional" in the sense that they are routinely used and have a very high rate of success.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va. 367–372, (1982)) and in Duncan et al., "The Production of Callus Capable of Plant Regeneration from Immature Embryos of Numerous *Zea Mays* Genotypes," 165 *Planta* 322:332 (1985). Thus, another aspect of this invention is to provide cells which upon growth and differentiation produce corn plants having the physiological and morphological characteristics of inbred corn line KW4773.

The utility of inbred corn line KW4773 also extends to crosses with other species. Commonly, suitable species will be of the family Graminaceae, and especially of the genera Zea, Tripsacum, Croix, Schlerachne, Polytoca, Chionachne, and Trilobachne, of the tribe Maydeae. Potentially suitable for crosses with KW4773 may be the various varieties of grain sorghum, *Sorghum bicolor* (L.) Moench.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as Atransgenes. Over the last fifteen to twenty years several methods for producing transgenic plants have been developed, and the present invention, in particular embodiments, also relates to transformed versions of the claimed inbred line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed corn plants, using transformation methods as described below to incorporate transgenes into the genetic material of the corn plant(s).

Expression Vectors for Corn Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990<Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984). Another approach to the identification of relatively rare transformation events has been use of a gene that encodes a dominant constitutive regulator of the *Zea mays* anthocyanin pigmentation pathway. Ludwig et al., *Science* 247:449 (1990).

Recently, in vivo methods for visualizing GUS activity that do not require destruction of plant tissue have been made available. Molecular Probes publication 2908, Imagene GreenJ, p. 1–4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in procaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, A promoter includes reference to a region of DNA upstream from the start of transcription and involved in recognition and binding of RNA polymerase and other proteins to initiate transcription. A plant promoter is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as A tissue preferred. Promoters which initiate transcription only in certain tissue are referred to as tissue specific. A cell type specific promoter primarily drives expression in certain cell types in one or more organs, for example, vascular cells in roots or leaves. An inducible promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of non-constitutive promoters. A constitutive promoter is a promoter which is active under most environmental conditions.

A. Inducible Promoters

An inducible promoter is operably linked to a gene for expression in corn. Optionally, the inducible promoter is operably linked to a nucleotide sequence encoding a signal sequence which is operably linked to a gene for expression in corn. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Meft et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in corn or the constitutive promoter is operably linked to a nucleotide sequence encoding a signal sequence which is operably linked to a gene for expression in corn.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO96/30530.

C. Tissue-specific or Tissue-preferred Promoters

A tissue-specific promoter is operably linked to a gene for expression in corn. Optionally, the tissue-specific promoter is operably linked to a nucleotide sequence encoding a signal sequence which is operably linked to a gene for expression in corn. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217:240–245 (1989)); a pollen-specific promoter such as that from Zm13 (Guerrero et al., *Mol. Gen. Genetics* 244:161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P.S., Master's Thesis, Iowa State University (1993), Knox, C., et al., AStructure and Organization of Two Divergent Alpha-Amylase Genes from Barley, *Plant Mol. Biol.* 9:3–17 (1987), Lerner et al., *Plant Physiol.* 91:124–129 (1989), Fontes et al., *Plant Cell* 3:483–496 (1991), Matsuoka et al., *Proc. Natl. Acad. Sci.* 88:834 (1991), Gould et al.,*J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is corn. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology *CRC Press, Boca Raton* 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., *Science* 266:789 (1994) (cloning of the tomato Cf-9 gene for resistance to *Cladospodum fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclose by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in Diploptera puntata). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanaceanum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A development-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes That Confer Resistance to a Herbicide, For Example:

A. A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+ genes) and a benzonitrile (nitrilase gene). Przibilla et al., *Plant Cell* 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such as:
  A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).
  B. Decreased phytate content
    1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an *Aspergillus niger* phytase gene.
    2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).
  C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Corn Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. Agrobacterium-mediated Transformation

One method for introducing an expression vector into plants is based on the natural transformation system of Agrobacterium. See, for example, Horsch et al., *Science* 227:1229 (1985). A. tumefaciens and A. rhizogenes are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of Agrobacterium vector systems and methods for Agrobacterium-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer

Despite the fact the host range for Agrobacterium-mediated transformation is broad, some major cereal crop species and gymnosperms have generally been recalcitrant to this mode of gene transfer, even though some success has recently been achieved in rice and corn. Hiei et al., *The Plant Journal* 6:271–282 (1994) and U.S. Pat. No. 5,591,616 issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495–1505 (1992) and Spencer et al., *Plant Mol. Biol.* 24:51–61 (1994).

Following transformation of corn target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular corn line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term inbred corn plant is used in the context of the present invention, this also includes any single gene conversions of that inbred. The term single gene converted plant as used herein refers to those corn plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental corn plants for that inbred. The parental corn plant which contributes the gene for the desired characteristic is termed the nonrecurrent or donor parent. This terminology refers to the fact that the nonrecurrent parent is used one time in the backcross protocol and therefore does not recur. The parental corn plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Industrial Applicability

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs and poultry.

Industrial uses of corn include production of ethanol, corn starch in the wet-milling industry and corn flour in the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds and other mining applications.

Plant parts other than the grain of corn are also used in industry, for example: stalks and husks are made into paper and wallboard and cobs are used for fuel and to make charcoal.

The seed of inbred corn line KW4773, the plant produced from the inbred seed, the hybrid corn plant produced from the crossing of the inbred, hybrid seed, and various parts of the hybrid corn plant and transgenic versions of the foregoing, can be utilized for human food, livestock feed, and as a raw material in industry.

DEPOSIT INFORMATION

A deposit of seed of the corn inbred, KW4773, of this invention is maintained by AgReliant Genetics, LLC 972 County Road 500 East, Ivesdale, Ill. 61851. Access to this deposit will be available during the pendency of this application to persons determined by the Commissioner of Patent and Trademarks to be entitled thereto under 37 CRF 1.14 and 35 USC 122. Upon allowance of any claims in this application, all restrictions on the availability to the public of the inbred will be irrevocably removed by affording access to a deposit of at least 2,500 seeds of the same inbred with the American Type Culture Collection (ATCC), 10801 University Boulevard, Manassas, Va. 20110.

Although the forgoing invention has been described in some detail by way of illustration and example for purpose of clarity and understanding, it will be obvious that certain changes and modifications may be practiced within the scope of the invention, as limited only by the scope of the appended claims.

What is claimed is:

1. Seed of corn inbred line designated KW4773, representative seed of said line having been deposited under ATCC Accession No.

2. A corn plant, or parts thereof, produced by growing the seed of claim 1.

3. Pollen of the plant of claim 2.

4. An ovule of the plant of claim 2.

5. A corn plant, or parts thereof, having all of the physiological and morphological characteristics of the corn plant of claim 2.

6. A tissue culture of regenerable cells from the corn plant of claim 2.

7. A tissue culture according to claim 6, wherein cells of the tissue culture or protoplasts produced from the tissue culture are from a tissue selected from the group consisting of leaves, pollen, embryos, roots, root tips, anthers, silks, flowers, kernels, ears, cobs, husks, and stalks.

8. A corn plant regenerated from the tissue culture of claim 6, wherein the regenerated plant has all the morphological and physiological characteristics of inbred line KW4773.

9. A method for producing a hybrid corn seed comprising crossing a first inbred parent corn plant with a second inbred parent corn plant and harvesting the resultant hybrid corn seed, wherein said first inbred parent corn plant or said second parent corn plant is the corn plant of claim 2.

10. A method for producing an herbicide resistant corn plant comprising transforming the corn plant of claim 2 with a transgene that confers herbicide resistance.

11. An herbicide resistant corn plant produced by the method of claim 10.

12. A method of producing an insect resistant corn plant comprising transforming the corn plant of claim 2 with a transgene that confers insect resistance.

13. An insect resistant corn plant produced by the method of claim 12.

14. A method of producing a disease resistant corn plant comprising transforming the corn plant of claim 2 with a transgene that confers disease resistance.

15. A disease resistant corn plant produced by the method of claim 14.

16. A method of producing a corn plant with decreased phytate content comprising transforming the corn plant of claim 2 with a transgene encoding phytase.

17. A corn plant with decreased phytate content, produced by the method of claim 16.

18. A method of producing a corn plant with modified fatty acid or carbohydrate metabolism comprising transforming the corn plant of claim 2 with one or more transgenes encoding a protein selected from the group consisting of stearyl-ACP desaturase, fructosyltransferase, levansucrase, alpha-amylase, invertase, and starch branching enzyme.

19. A corn plant with modified fatty acid or carbohydrate metabolism produced by the method of claim 18.

20. A method of producing a male-sterile corn plant comprising transforming the corn plant of claim 2 with a transgene that confers male sterility.

21. A male-sterile corn plant produced by the method of claim 20.

* * * * *